(12) United States Patent
Jarvis et al.

(10) Patent No.: US 8,921,092 B2
(45) Date of Patent: *Dec. 30, 2014

(54) SYSTEM AND METHOD FOR ELECTROPORATING A SAMPLE

(71) Applicant: Applied Biosystems, LLC, Carlsbad, CA (US)

(72) Inventors: Richard Jarvis, Austin, TX (US); Mike Byrom, Austin, TX (US); Dmitriy Ovcharenko, Austin, TX (US)

(73) Assignee: Applied Biosystems LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/765,671

(22) Filed: Feb. 12, 2013

(65) Prior Publication Data

US 2014/0057337 A1 Feb. 27, 2014

Related U.S. Application Data

(60) Continuation of application No. 12/760,526, filed on Apr. 14, 2010, now Pat. No. 8,383,394, which is a continuation of application No. 12/123,619, filed on May 20, 2008, now Pat. No. 8,017,399, which is a division of application No. 11/130,884, filed on May 17, 2005, now Pat. No. 7,393,681, which is a continuation of application No. 10/863,102, filed on Jun. 8, 2004, now Pat. No. 6,897,069.

(51) Int. Cl.
*C12M 1/42* (2006.01)
*C12M 1/00* (2006.01)
*C12N 15/86* (2006.01)
*A61K 48/00* (2006.01)

(52) U.S. Cl.
CPC ............. *C12M 45/07* (2013.01); *C12M 35/02* (2013.01); *C12N 15/86* (2013.01); *A61K 48/00* (2013.01); *C12N 2710/16632* (2013.01); *C12N 2710/16643* (2013.01); *C12N 2830/00* (2013.01); *C12N 2830/008* (2013.01)
USPC .......... 435/285.2; 435/450; 435/461; 435/470

(58) Field of Classification Search
None
See application file for complete search history.

(56) References Cited

U.S. PATENT DOCUMENTS

| | | | |
|---|---|---|---|
| 5,007,995 A | 4/1991 | Takahashi et al. | |
| 6,241,701 B1 | 6/2001 | Hofmann | |
| 6,352,853 B1 | 3/2002 | King et al. | |
| 6,627,421 B1 | 9/2003 | Unger et al. | |
| 6,628,382 B2 | 9/2003 | Robertson | |
| 6,897,069 B1 * | 5/2005 | Jarvis et al. | 435/461 |
| 6,936,462 B1 | 8/2005 | Owen et al. | |
| 7,384,781 B2 | 6/2008 | Moyle et al. | |
| 7,393,681 B2 | 7/2008 | Jarvis et al. | |
| 7,456,012 B2 | 11/2008 | Ryttsén et al. | |
| 7,678,564 B2 | 3/2010 | Muller-Hartmann et al. | |
| 8,017,399 B2 | 9/2011 | Jarvis et al. | |
| 8,101,401 B2 | 1/2012 | Muller-Hartmann et al. | |
| 8,383,394 B2 * | 2/2013 | Jarvis et al. | 435/285.2 |
| 2003/0009148 A1 | 1/2003 | Hayakawa | |
| 2003/0070923 A1 | 4/2003 | Schroeder et al. | |
| 2005/0164161 A1 | 7/2005 | Augustine et al. | |
| 2008/0213854 A1 | 9/2008 | Wirth et al. | |
| 2010/0196998 A1 | 8/2010 | Jarvis et al. | |
| 2011/0263005 A1 | 10/2011 | Chang et al. | |

FOREIGN PATENT DOCUMENTS

| | | |
|---|---|---|
| EP | 0338667 | 10/1989 |
| JP | 63049070 | 3/1988 |
| JP | 11290058 | 10/1999 |
| JP | 2007167006 | 7/2007 |
| JP | 2008502356 | 1/2008 |
| WO | WO99/24110 | 5/1999 |
| WO | WO00/63408 | 10/2000 |
| WO | WO0233066 | 4/2002 |
| WO | WO03/057819 | 7/2003 |
| WO | WO2004/031353 | 4/2004 |
| WO | WO2005/123931 | 12/2005 |
| WO | WO2006/001614 | 1/2006 |
| WO | WO2008/051169 | 5/2008 |

OTHER PUBLICATIONS

Dong et al., "Monitoring diclofenac sodium in single human erythrocytes introduced by electroporation using capillary zone electrophoresis with electrochemical detection", *Electrophoresis*, vol. 22, No. 13, Aug. 2001, 2786-2792.

Hu et al., "Inhibition of Retroviral Pathogenesis by RNA Interference", *Current Biology*, vol. 12, Issue 15, Aug. 6, 2002, 1301-1311.

Lin et al., "Electroporation microchips for continuous gene transfection", *Sensors and Actuators B*, vol. 79, 2001, 137-143.

Nolkrantz et al., "Electroporation of Single Cells and Tissues with an Electrolyte-filled Capillary", *Analytical Chemistry*, vol. 73, Issue 18,, Sep. 15, 2001, 4469-4477.

Osumi et al., "Gene Transfer into Cultured Mammalian Embyos by Electroporation", *Methods*, vol. 24, 2001, 35-42.

Speyer et al., "A Simple and Effective Electroporation Apparatus", *Biotechniques*, vol. 8, No. 1, Jan. 1980, 28-30.

Speyer, "Multi-Sample Electroporation", *Bio Techniques*, vol. 8, No. 5, May 1990, 508.

U.S. Appl. No. 11/130,884, Notice of Allowance mailed Mar. 25, 2008.

(Continued)

*Primary Examiner* — Jim Ketter
(74) *Attorney, Agent, or Firm* — Applied Biosystems LLC

(57) ABSTRACT

A system and method are described for electroporating a sample that utilizes one or more sets of electrodes that are spaced apart in order to hold a surface tension constrained sample between the electrodes. The first electrode is connected to the lower body of the system while the second electrode is connected to the upper body. Both electrodes are connected to a pulse generator. Each electrode has a sample contact surface such that the first electrode and the second electrode may be positioned to hold a surface tension constrained sample between the two sample contact surfaces and the sample may receive a selected electric pulse.

7 Claims, 6 Drawing Sheets

(56) References Cited

OTHER PUBLICATIONS

U.S. Appl. No. 11/130,884, Notice of Drawing Inconsistency with Specification mailed Apr. 22, 2008.
U.S. Appl. No. 11/130,884, Office Action mailed Oct. 23, 2007.
U.S. Appl. No. 11/130,884, Response to Notice of Drawing Inconsistency with Specification and Amendment Under Rule 312 filed May 20, 2008.
U.S. Appl. No. 11/130,884, Response to Oct. 23, 2007 Office Action filed Jan. 9, 2008.
U.S. Appl. No. 11/130,884, Response to Rule 312 Communication mailed May 27, 2008.
U.S. Appl. No. 12/123,619, Notice of Allowance mailed Jan. 13, 2011.
U.S. Appl. No. 12/123,619, Office Action mailed Feb. 20, 2009.
U.S. Appl. No. 12/123,619, Office Action mailed May 26, 2010.
U.S. Appl. No. 12/123,619, Office Action mailed Oct. 15, 2009.
U.S. Appl. No. 12/123,619, Response to Feb. 20, 2009 Office Action filed Jun. 15, 2009.
U.S. Appl. No. 12/123,619, Response to May 26, 2010 Office Action filed Oct. 26, 2010.
U.S. Appl. No. 12/123,619, Response to Oct. 15, 2009 Office Action filed Feb. 11, 2010.

* cited by examiner

SYSTEM AND METHOD FOR ELECTROPORATING A SAMPLE

RELATED APPLICATION

This application is continuation of U.S. application Ser. No. 12/760,526 filed Apr. 14, 2010 (now U.S. Pat. No. 8,383, 394), which is continuation of U.S. application Ser. No. 12/123,619 filed May 20, 2008 (now U.S. Pat. No. 8,017, 399), which is a divisional of U.S. application Ser. No. 11/130,884 filed May 17, 2005 (now U.S. Pat. No. 7,393, 681), which is a continuation of U.S. application Ser. No. 10/863,102 filed Jun. 8, 2004 (now U.S. Pat. No. 6,897,069), the contents of which are hereby incorporated in their entirety by reference.

TECHNICAL FIELD OF THE INVENTION

The present disclosure relates in general to systems and method for processing biological samples and more particularly to an electroporation system and method of use thereof.

BACKGROUND OF THE INVENTION

Gene silencing using small interfering RNAs (siRNAs) has become a powerful method for studying gene function. The use of siRNAs often accelerates applications such as target validation, gene discovery, tissue engineering and gene therapeutic approaches. siRNAs are often used by researchers to reduce the expression of specific genes in mammalian cells. Researchers may design siRNAs or purchase validated siRNAs for their target of interest and transfect them into culture cells. Human primary cells are often desired for such experiments because they are more similar to their in vivo counterparts than are immortalized cells. However, common chemical-based transfection methods that work well for cell lines often fail to transfect primary cells.

One technique that has been used with considerable success to deliver siRNA to cells (including primary cells) is electroporation. Electroporation involves applying an electric field pulse to cells to induce the formation of microscopic pores (electropores) in the cell membrane allowing molecules, ions, and water to traverse the destabilized cell membrane. The transfer of nucleic acids to cells by electroporation is an effective method for achieving high efficiency transfections in vitro and in vivo. Under specific pulse conditions, the electropores reseal and the "electroporated" cells recover and continue to grow.

Successfully delivering functional siRNA to cells typically requires that several optimum electroporation conditions be determined. To determine optimal electroporation conditions, a comprehensive set of data is usually generated from a collection of different transfection conditions including: testing various electrical wave-forms, types of electroporation buffers, different temperatures, and cell densities. Careful examination of these parameters for a new cell type typically requires lengthy processing times using standard cuvette-based electroporation methods.

In some electroporation environments successful delivery and cell viability depend on multiple electrical parameters such as: field strength (primarily voltage in relation to gap width), pulse length, and number of pulses. Determining the optimum electroporation conditions for delivering siRNA is typically a lengthy and costly process. Additional experimentation may then be carried out to test multiple different siRNAs in various amounts to modulate the target gene (or genes) to a desired level of expression.

A significant drawback to electroporation is the format in which it is conducted. Commercially available electroporation instruments use sample cuvettes and require significant amounts of preparation. This limits the number and types of experiments that can be performed, incurs the expense of using a specialized cuvette to deliver the desired pulse to the sample, and requires significant time and effort to deposit samples within the cuvettes, deposit the cuvettes in an appropriate apparatus, and to remove the electroporated sample from the cuvette.

SUMMARY OF THE INVENTION

Therefore a need has arisen for a system and method for facilitating the electroporation of a sample that does not require a cuvette.

A further need has arisen for a system and method for efficiently electroporating multiple samples.

In accordance with teachings of the present disclosure, a system and method are described for electroporating a sample that reduces or eliminate drawbacks associated with previous electroporation systems and methods. An electroporation system is disclosed that includes one or more sets of electrodes that are spaced apart in order to hold a surface tension constrained sample between the electrodes. The system may include multiple sets of electrodes in order to allow multiple samples to be electroporated simultaneously.

In one aspect an electroporation system is disclosed that includes a housing having a lower body and an upper body. A first removable electrode is connected to the lower body. A second removable electrode is connected to the upper body. Both electrodes may receive an electric pulse from a pulse generator. Each removable electrode has a sample contact surface and the first removable electrode and the second removable electrode may be positioned such that a surface tension constrained sample may be confined between the two sample contact surfaces.

In another aspect, an electrode array is disclosed that includes an electrode base that may conductively couple to an electroporation body. The electrode base has multiple sample contact surfaces formed thereon. The electrode is able to receive a pulse from a pulse generator and each of the sample contact surfaces is sized to hold an electroporation sample.

In another aspect an electroporation system includes a housing that has a lower body and an upper body. A first electrode array is attached to the lower body and a second electrode array is attached to the upper body. The first electrode array has multiple lower sample contact surfaces and the second electrode array has multiple upper sample contact surfaces that correspond to the multiple lower sample contact surfaces. The lower body and the upper body are positioned to confine a surface tension constrained sample between each of the corresponding pairs of upper contact surfaces and lower contact surfaces. The electrode arrays may receive an electric pulse from a pulse generator to facilitate the electroporation of the samples.

In yet another aspect, a method for electroporating a sample comprises positioning the upper body of an electroporation apparatus in an access position. Samples that are to be electroporated are then deposited on the multiple lower sample contact surfaces of the electrode array of the lower body. The upper body is then moved into an operational position such that corresponding upper sample contact surfaces contact the samples resting on the lower sample contact surfaces. Each sample is confined between an upper sample contact surface and a lower sample contact surface by the surface tension of each sample. A selected electric pulse is then passed between the lower electrode and the upper electrode, sufficient to electroporate each sample.

The present disclosure includes a number of important technical advantages. One technical advantage is to provide electrode pairs with contact surfaces positioned to confine a surface tension constrained sample therebetween. This allows for electroporation to be conducted without the use of cuvettes. Another technical advantage is to provide electrode arrays that have multiple contact surfaces formed thereon. This allows for multiple samples to be electroporated simultaneously. Additional advantages will be apparent to those of skill in the art in the description, FIGURES, and claims below.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

Preferred embodiments and their advantages are best understood by reference to FIGS. 1 through 15, wherein like numbers are used to indicate like and corresponding parts.

The novel systems described herein offer significant improvement in the practical application of electroporation and thereby promote the use of siRNA molecules to more cell types and to researchers previously unfamiliar with electroporation. The electroporation systems are designed to constrain a sample based on the sample's surface tension rather than hardware geometry alone (as compared with cuvette-based electroporation methods). The disclosed systems simplify the overall electroporation process and promote the more rapid determination of optimum electroporation conditions with reasonable cost and time.

Figure 1:
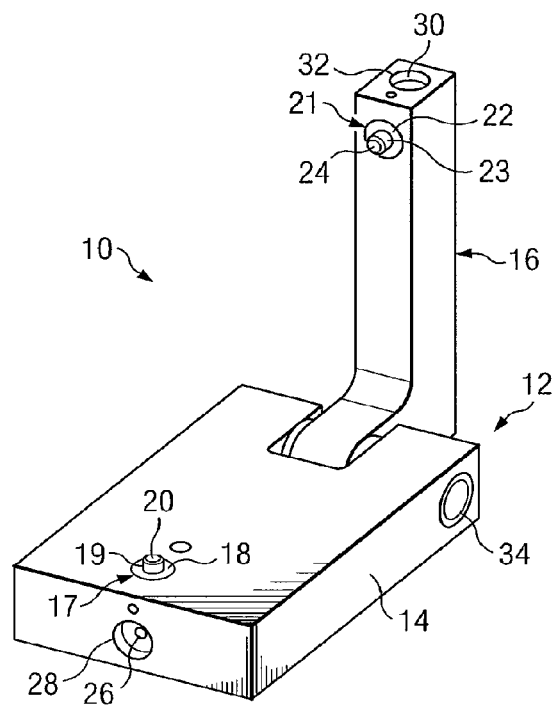
FIG. 1 is an electroporation system shown in an access position.
Figure 2:
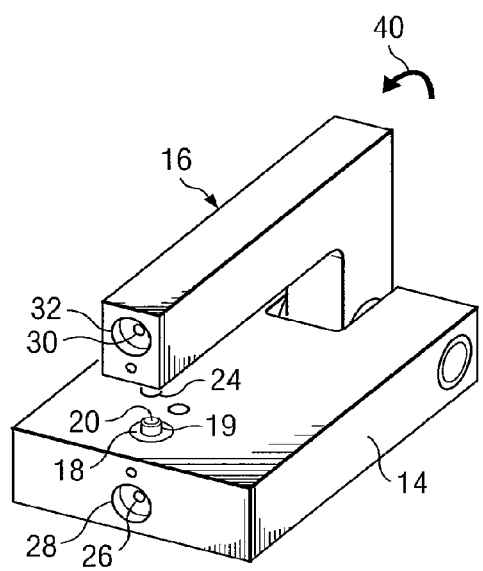
FIG. 2 is an electroporation system shown in an operational position.

Now referring to FIG. 1, an electroporation system 10 is shown. Electroporation system 10 includes housing 12 that generally includes lower body 14 and upper body 16. Lower body 14 and upper body 16 are both constructed of nonconductive materials such as, for example acetal plastic. In the present embodiment, upper body 16 is pivotally connected to lower body 14 at pivot 34. In the present embodiment this allows upper body 16 to rotate between a generally vertical access position, as shown, and an operational position as shown in FIG. 2.

Electroporation system 10 further includes first electrode 18 inserted within electrode aperture 17 formed in lower body 14 as well as second electrode 22 disposed within electrode aperture 21. First electrode 18 may also be referred to as a "removable electrode", "disposable electrode" or a "lower electrode" herein. Second electrode 22 may also be referred to as a "removable electrode", "disposable electrode" or an "upper electrode" herein. First and second electrodes 18 and 22 are preferably removable from electrode apertures 17 and 21 such that they may be cleaned, replaced, or disposed of following an electroporation operation. In alternate embodiments, first electrode 18 and second electrode 22 may be selectively fixed to lower body 14 and upper body 16 using any suitable attachment mechanism that also allows first electrode 18 and second electrode 22 to be conductively connected to a pulse generator.

In the present embodiment first electrode 18 has a generally cylindrical body and a sample contact structure 19 formed at one end thereof. Similarly, second electrode 22 includes a sample contact structure 23, including second sample contact surface 24 (which may also be referred to as the upper sample contact surface), formed on one end thereof. The end of sample contact structure 23 that extends from upper body 16 forms second sample contact surface 24 (which may also be referred to as upper contact surface).

In the present embodiment first and second sample contact surfaces 20 and 24 are formed to correspond with one another, having substantially identical shapes. First and second sample contact surfaces 20 and 24 have substantially circular in shape and are substantially flat. First sample contact surface 20 is preferably sized to have a volume of sample appropriate for electroporation deposited thereon. Second sample contact surface 24 is correspondingly sized to contact the sample for carrying out the electroporation operation. In the present preferred embodiment first sample contact surface 20 is sized to hold a sample between approximately ten microliters and two hundred microliters. In one embodiment, this corresponds to first sample contact surface 20 having a diameter between approximately two millimeters and approximately twelve millimeters. Additionally, the sample size supportable for electroporation between first sample contact surface 20 and second sample contact surface 24 is further dependent upon gap-width between the contact surfaces during electroporation. As the gap width increases, the sample size supported between first sample contact surface 20 and second sample contact surface 24 increases. However, if gap width increases too much, the surface tension of the sample will be unable support the sample between the contact surfaces. Accordingly, the appropriate upper limit of gap width between first contact surface 20 and second contact surface 24 will vary depending on the surface area and geometry of contact surfaces 20 and 24 and the properties of the sample being processed. In preferred embodiments, electroporation sample 10 may support a gap width between first contact surface 20 and second contact surface 24 in the range of 0.01 millimeter and approximately ten (10) millimeters.

Figure 5:
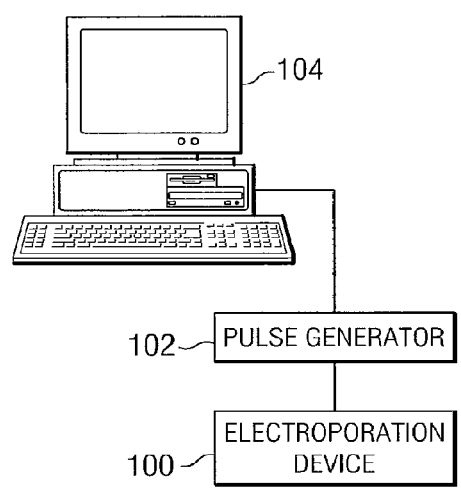
FIG. 5 shows an electroporation system including a pulse generator and a monitoring system.

First electrode 18 and second electrode 22 further include contacts 26 and 30 to facilitate a conductive connection with a pulse generator (as shown in FIG. 5). Contacts 26 and 30 are formed to align with access apertures 28 and 32 formed in lower body 14 and upper body 16, respectively. Connectors (not expressly shown) associated with a pulse generator may pass through access apertures 28 and 32 to contact first electrode contact 26 and second electrode contact 30. This preferably allows for fast and convenient connection and disconnection with first electrode 18 and second electrode 22 which is particularly convenient for in instances where electrodes 18 and 22 are frequently removed and replaced.

Now referring to FIG. 2, electroporation system 10 is shown in an operational position. As shown, upper arm 16 has been rotated in the direction of arrow 40 to an operational position where first sample contact surface 20 and second sample contact surface are in substantially vertical alignment and slightly displaced from one another in order to hold a surface tension constrained sample therebetween.

In alternate embodiments, the access position may include any appropriate position where upper body 16 is positioned away from lower body 14. This may include an access position (not expressly shown) where upper body 16 is simply raised vertically with respect to lower arm 14 such that sample contact surface 20 is accessible to a user of system 10.

Figure 4:
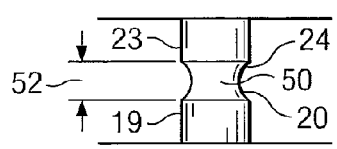
FIG. 4 shows a surface tension constrained sample confined between two electrodes.

In the present embodiment, as upper body 16 (which may also be referred to as a movable arm assembly or a swing arm herein) is moved in the direction of arrow 40, upper body 16 is moved to allow second sample contact surface 24 to substantially fully contact a sample resting on first contact surface 20. This typically requires that second contact surface 24 is positioned in slightly closer proximity to first contact surface 20 than in the operational position, thereby "pushing down" slightly on the sample. This position (not expressly shown) may be referred to herein as the "sample contact position". The sample contact position ensures that both sample contact surfaces 20 and 24 are in contact with the sample. The upper arm is then moved to the operational position (as shown in FIG. 4) wherein the surface tension of the sample acts to confine the sample between the first contact surface 20 and the second contact surface 24 without the use of a cuvette.

After a samples is confined between first contact surface 20 and second contact surface 22, an electric pulse is passed through the sample. The electrical field generated between the two facing sample contact surfaces 20 and 24 mediates reversible membrane permeabilization of the suspended cells within the sample, preferably allowing one or more desired elements such as, for example, a nucleic acid, protein or other biologically active compound, siRNA, messenger RNA (mRNA), or any other desired molecule included within the sample solution to traverse into the cells. After the electric pulse is complete, the cell membranes restabilize with the desired molecules delivered therein. Upper body 16 may then be moved back to the access position. This step is typically performed slowly such that the sample may disengage from second sample contact surface 24 and rests completely on first sample contact surface 20. The sample may then be removed from first sample contact surface 20, such as via a pipette, for subsequent use such as being transferred into a culturing vessel. In the event that some of the sample remains attached to second contact surface 24, such sample may also be removed by pipette.

Figure 6:
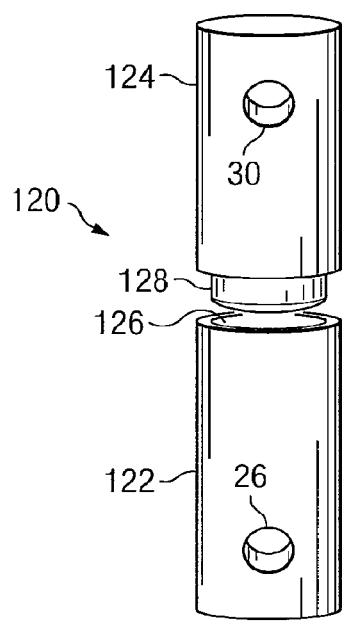
FIG. 6 is an electrode pair having corresponding concave and convex surfaces.
Figure 7:
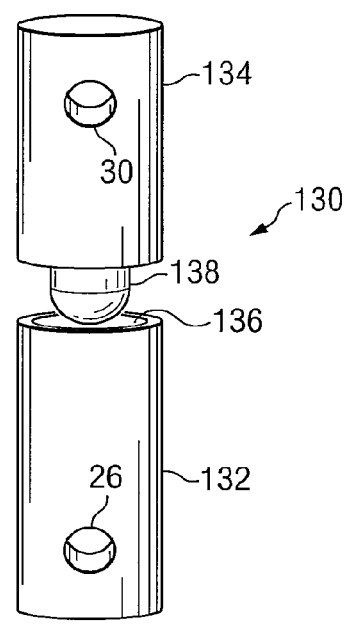
FIG. 7 is an electrode pair having corresponding concave and convex surfaces.

In some embodiments, electrodes 18 and 22 may then be cleaned to remove any residual sample therefrom. In other embodiments, electrodes 18 and 22 are preferably removed and disposed of and replace with replacement electrodes. Replacement electrodes may be identical to electrodes 18 and 22. Alternatively, replace electrodes may vary in the size and/or shape of the contact surfaces 20 and 24. In one embodiment, a series of electrode pairs may be provide that have a range of sample contact surface sizes in order to facilitate electroporation of various sized samples. Additional alternative embodiments of electrode pairs are shown in FIGS. 6 and 7.

Electroporation system 10 provides a convenient and efficient electroporation apparatus that may be particularly suited for laboratories and other users that do not require a high throughput of samples, but regularly need for transfection of samples. Electroporation system 10 facilitates such transfection without the use of cuvettes.

Figure 3:
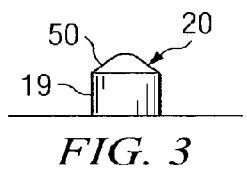
FIG. 3 is an electrode with a sample deposited thereon.

FIG. 3 shows first electrode 18 when electroporation system is in an access position. As shown, sample 50 is deposited on sample contact surface 20 atop sample contact structure 19 of first electrode 18. Both adherent and suspended varieties of multiple primary and cultured immortalized cell types may be examined. These may include, but are not limited to HUVEC, hMSC, PC12, human B or T cells, human or mouse Neuronal, Hela, MCF-7, K562, or Jurkat cells. In Some preferred embodiments the siRNAs to be used may preferably target housekeeping genes or other highly expressed genes, or any gene or regulatory element relevant to a user.

FIG. 4 shows the sample contact structure 19 of first electrode 18 and sample contact structure 23 of second electrode 22 in an operational position. The surface tension of sample 50 confines it between first sample contact surface 20 and second sample contact surface. As shown, first sample contact surface 20 and second sample contact surface 24 are positioned a selected distance 52 which may also referred to as gap width, apart from each other.

FIG. 5 shows an electroporation system including pulse generator 102 and a monitoring system 104. As shown, electroporation device 100 is conductively couple to pulse generator 102. Pulse generator 102 selectively provides an electric pulse to one or more samples held within electroporation devices 100. Any suitable pulse generator may be employed including, for example, a BTX Electro Square Porator ECM 830, a BioRad GenePulser Xcell, and a Cyto Pulse PA/40005 pulse generator. Pulse generator 102 is preferably connected to monitoring system 104. In the present embodiment, monitoring system is a computer system that includes software to set, manage and archive the applied waveforms produced by pulse generator 102.

FIGS. 6 and 7 shows electrode pairs 120 and 130, respectively. Electrode pair 120 includes first electrode 122 and second electrode 124. First electrode 122 includes contact 26 for connecting with a pulse generator and a concave sample contact surface 126. Second electrode 124 includes electrode contact 30 for connecting with a pulse generator and convex sample contact surface 128. Concave sample contact surface 126 forms a bowl a the end of electrode 122 for depositing a sample. Convex sample contact surface 128 is formed to substantially correspond with concave sample contact surface 126.

Electrode pair 130 includes first electrode 132 and second electrode 134. First electrode 132 includes contact 26 for connecting with a pulse generator and a concave sample contact surface 136. Second electrode 134 includes electrode contact 30 for connecting with a pulse generator and convex sample contact surface 138. Concave sample contact surface 136 forms a bowl a the end of electrode 132 for depositing a sample. Convex sample contact surface 138 is formed to substantially correspond with concave sample contact surface 136. As shown, convex sample contact surface 136 forms a substantially hemispherical bowl and concave sample contact surface 138 forms a substantially hemispherical protrusion.

Figure 8:
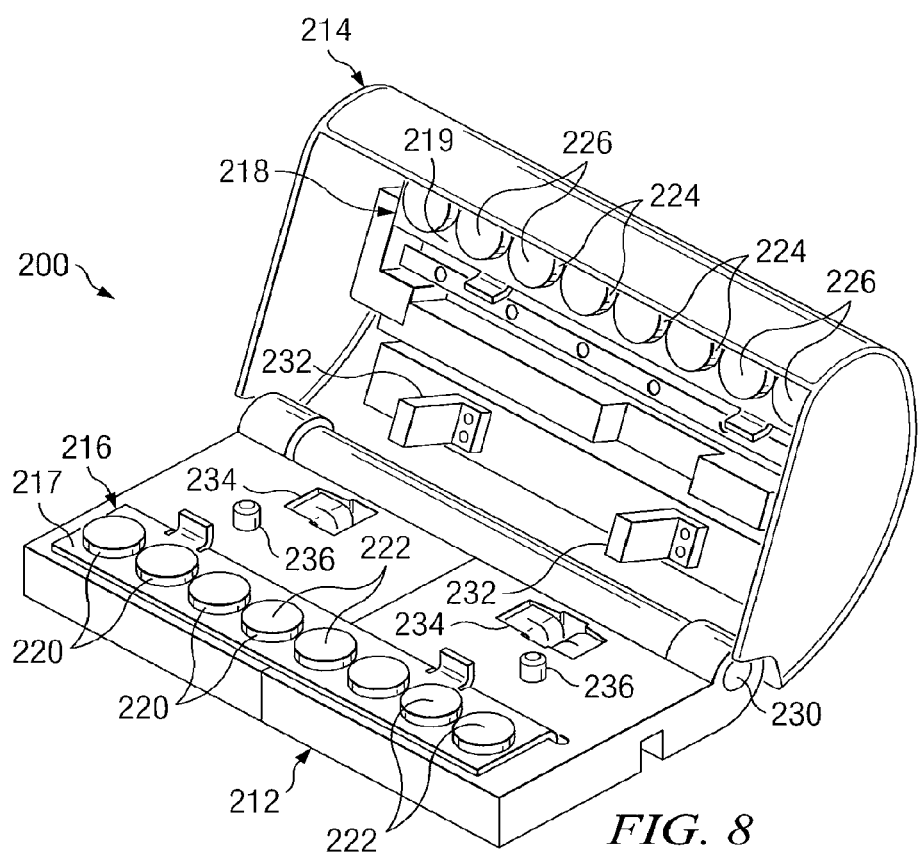
FIG. 8 is an eight sample electroporation system shown in an access position.

FIG. 8 shows an eight sample electroporation system depicted generally at 200 shown in an access or open position. Electroporation system 200 includes a housing 210 made up of lower body 212 (which may also be referred to as the "base") and upper body 214 (which may also be referred to as the "top"). First electrode array 216, which may also be referred to as an "lower" electrode array, is preferably coupled to lower body 212. First electrode array includes array body 217 with eight lower electrodes 220 formed thereon. Each of the lower electrodes 220 further includes a lower electrode sample contact surface 222. Second electrode array 218 is preferably coupled to upper body 214. Second electrode array includes array body 219 with eight upper electrodes 224 formed thereon. Each of the upper electrodes 224 includes an upper electrode sample contact surface 226.

Figure 9:
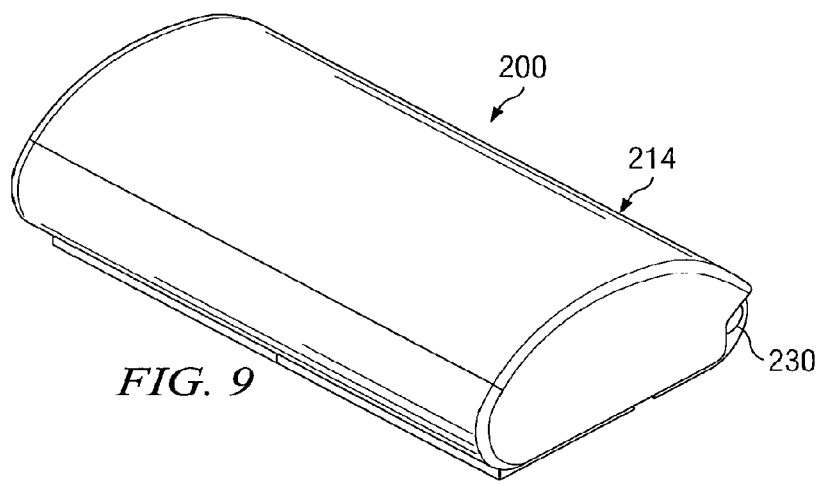
FIG. 9 is an eight sample electroporation system shown in an operational position.

Upper body 214 is preferably formed to enshroud and prevent physical access to lower electrode array 216 and upper electrode array 224 when upper body is moved to the operation position (as shown in FIG. 9). In the present embodiment, upper body 214 is pivotally connected with lower body 212 along pivot 230. Upper body further include interlock fangs 232 that protrude from upper body 214. Interlock fangs 232 correspond to interlock spring contacts 234. Fangs 232 are preferably inserted into and jumper together the two lower contact springs 234 when upper body 214 is moved into an operational position. Additionally, spring plungers 236 extend from lower body 212. Spring plungers 236 support top 214 during electroporation so that electrodes 220 and 224 are precisely spaced apart and are substantially parallel. Spring plungers 236 may further depress down when pressure is applied to top 214 such that upper electrodes 224 may be brought sufficiently close to contact sample that is resting on lower electrodes 220. Contacting the sample preferably forms a resilient surface tension constraining column between each upper sample contact surface 226 and lower electrode contact surface 222.

System 200 may preferably connected with a pulse generator such to operable to provide a desired pulse to samples held between pairs of upper sample contact surfaces 226 and lower electrode contact surfaces 222. Interlock fangs 232 and interlock spring contacts 234 preferably prevent pulses from an associated pulse generator to be delivered to electrode arrays 216 and 218 when the system is in an open or access position as shown. However, when upper body is moved into a closed position, as shown in FIG. 9, interlock fangs 232 serve to complete the circuitry required to deliver selected electric pulses to electrode arrays 216 and 218 necessary to electroporate samples held therebetween.

FIG. 9 shows eight sample electroporation system 200 shown in an operational position. As shown, upper body 214 prevents physical access to electrode arrays 216 and 218.

Figure 10:
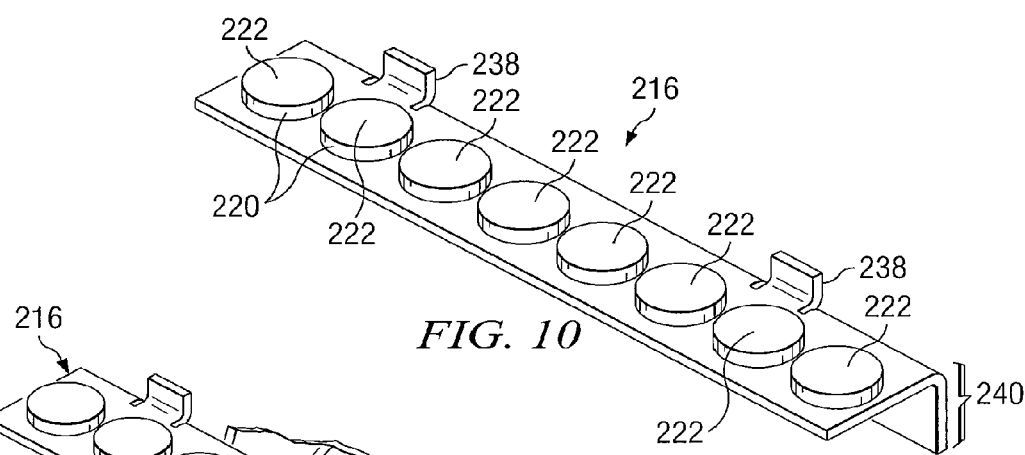
FIG. 10 is an electrode array according to teachings of the present disclosure.

FIG. 10 shows electrode array 216. Electrode array 216 includes array body 217 with eight lower electrodes formed thereon. In alternate embodiments lower electrodes may be fixed to array body 217. Each lower electrode is preferably formed to have sample contact surface 222 having a desired size and shape. Sample contact surface 222 in the present embodiment is a flat, circular surface. Alternate sample contact surface may incorporate non-circular and non-flat shape.

Array body 217 of electrode array 216 includes interface lip 240 extending generally perpendicular therefrom. Electrode body 217 further includes removal tabs 238 to facilitate installation and removal of array 216.

Figure 11:
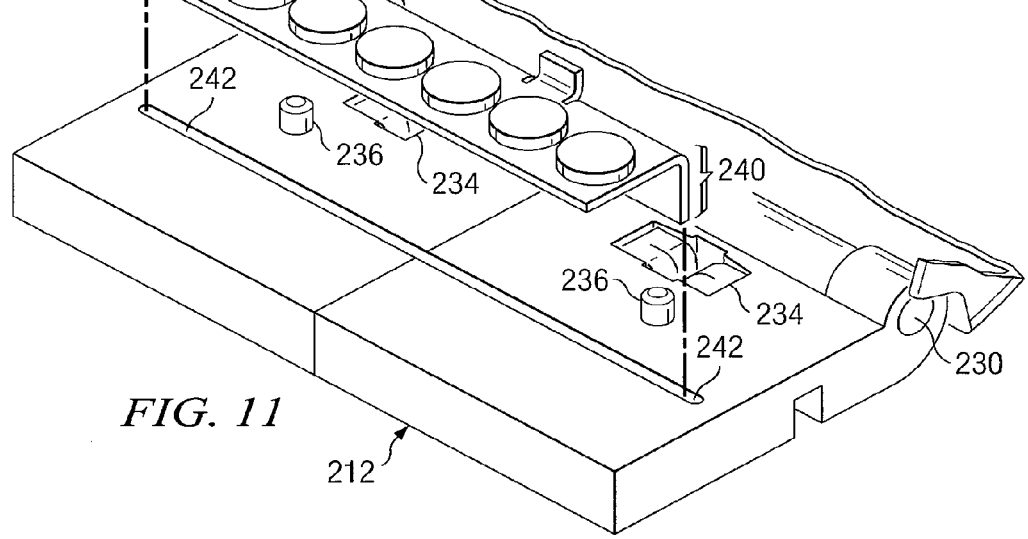
FIG. 11 is shows an electrode array interfacing with the lower body of an electroporation system.

FIG. 11 shows an eight sample electrode array 216 being interfaced with lower body 212. As shown, lower body includes interface slot 242 to allow electrode array to be conductively associated therewith. Interface lip 240 is preferably aligned with and inserted into interface slot 242. Spring contacts within interface slot 242 conductively connect with interface lip 240.

Figure 12:
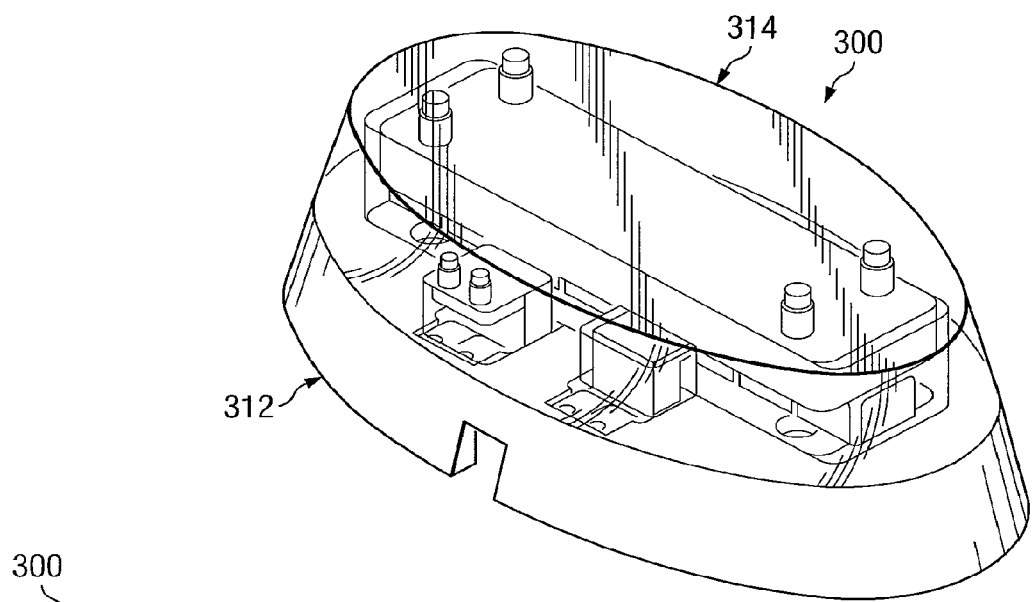
FIG. 12 shows an eight sample electroporation system in an operational position according to teachings of the present disclosure.
Figure 13:
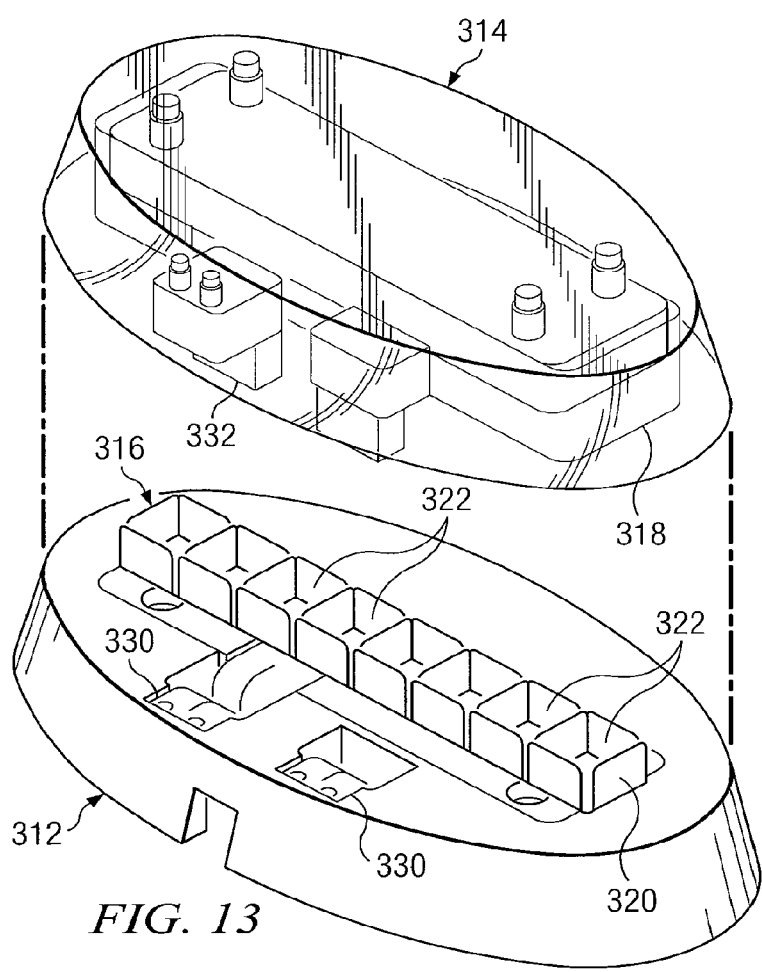
FIG. 13 shows an eight sample electroporation system in an access position according to teachings of the present disclosure.

FIG. 12 shows an eight sample electroporation system 300 in an operational position. As shown electroporation system 300 includes lower body (or "base" 312 and upper body 314 (or "top"). As shown in FIG. 13, which shows electroporation system 300 in an access position, lower body 312 and upper body 314 are physically distinct and may be physically separated. Lower body 312 includes electrode array 316 having eight electrodes 322 (each with sample contact surfaces). Each electrode is physically separated by insulated barriers 320. The insulated barriers (also referred to as "walls) serve to precisely space electrodes 322 and to maintain parallelism between corresponding electrodes.

Upper body 314 includes electrode array 318 that has electrodes corresponding to electrodes 322. Upper body 314 further includes interlocking fangs 332 extending therefrom and space to interface with interlock spring contacts 330. Interlocking fangs 332 and interlock spring contacts 330 function similarly to interlocking fangs 232 and interlock spring contacts 234 discussed above. As shown in the present embodiment, electrode arrays 316 and 318 are fixed to lower body 312 and upper body 314, respectively and are designed to be reused. In alternate embodiments, disposable arrays may be coupled lower body 312 and upper body 314 and may incorporate features for easy insertion and removal.

Figure 14:
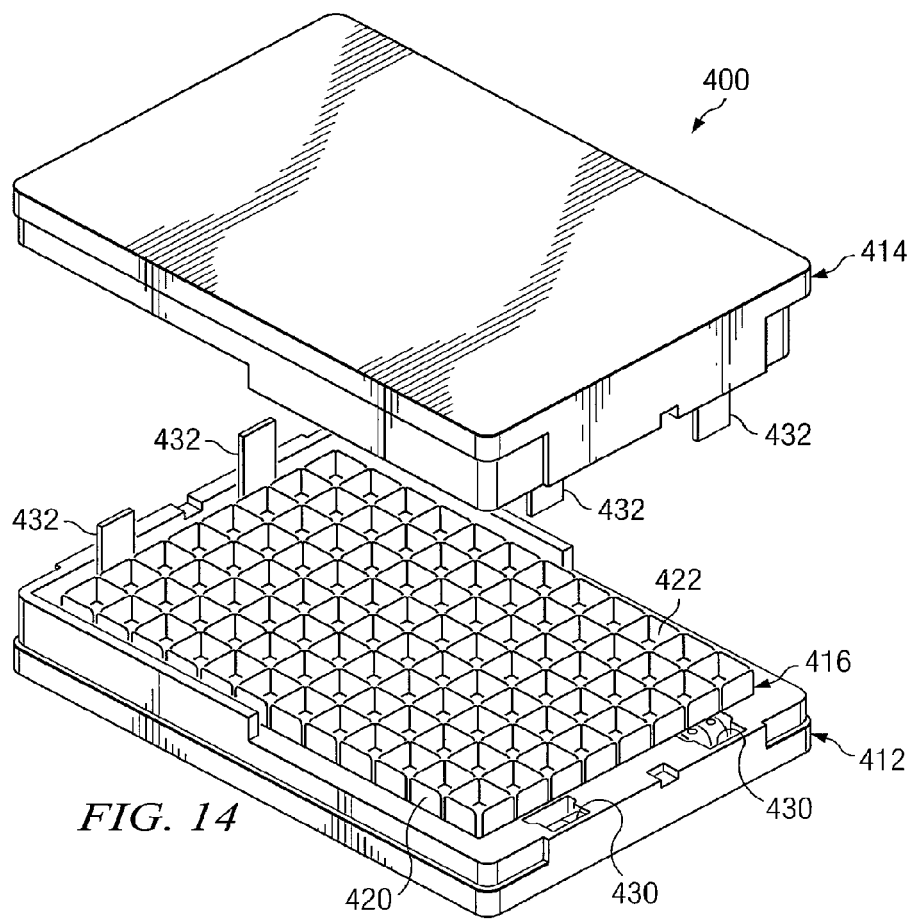
FIG. 14 shows a ninety-six sample electroporation system in an access position according to teachings of the present disclosure.
Figure 15:
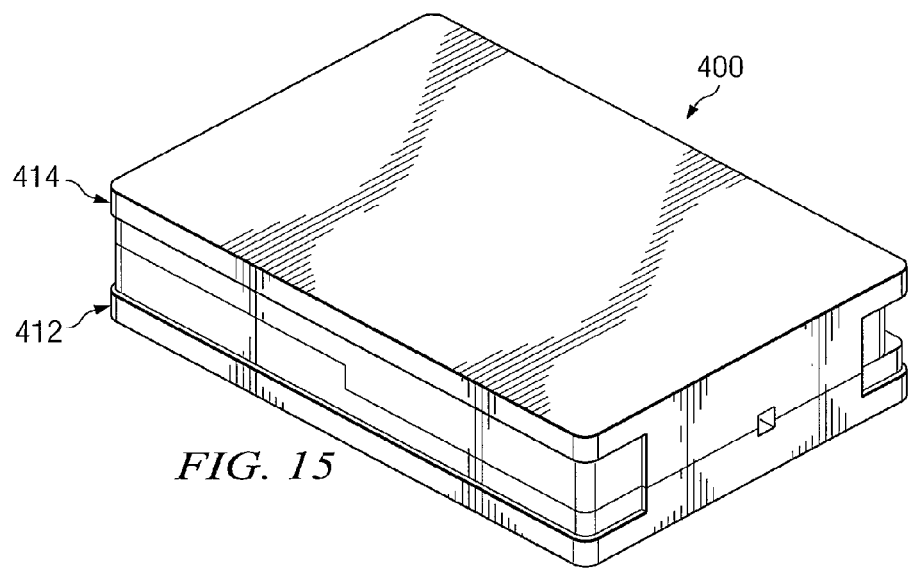
FIG. 15 shows a ninety-six sample electroporation system in an operational position according to teachings of the present disclosure.

A ninety-six sample electroporation system 400 is shown in an access position in FIG. 14 and in an operational position in FIG. 15. As shown electroporation system 400 includes lower body (or "base" 412 and upper body 414 (or "top"). Lower body 412 and upper body 414 are physically distinct and may be physically separated. Lower body 412 includes electrode array 416 having ninety-six electrodes 422 (each with sample a contact surfaces). Lower body 412 and upper body 414 correspond to precisely space electrodes 422 and to maintain parallelism with the corresponding upper electrodes.

Upper body 414 includes electrode array 418 that has upper electrodes (not expressly shown) corresponding to electrodes 422. Upper body 414 further includes interlocking fangs 432 as well as interlock spring contacts (not expressly shown) formed to mate with interlock fangs 432 projecting from lower body 412. Interlocking fangs 432 and interlock spring contacts 430 function similarly to interlocking fangs 232 and interlock spring contacts 234 discussed above. As shown in the present embodiment, electrode arrays 416 and 418 are fixed to lower body 412 and upper body 414, respectively and may be reused or may be removed and replaced.

Figure 16:
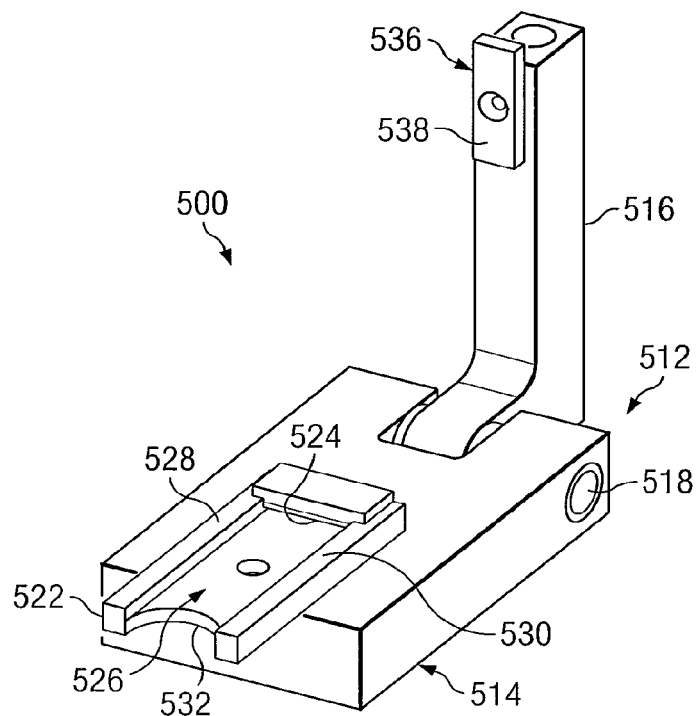
FIG. 16 shows an electroporation system with a lower and upper body with a conductive slide mounting structure on the lower body according to the teachings of the present disclosure.

Now referring to FIG. 16, an electroporation system 500 includes housing 512 that generally includes lower body 514 and upper body 516 is shown. Lower body 514 and upper body 516 are both preferably constructed of nonconductive materials. In the present embodiment, upper body 516 is pivotally connected to lower body 514 at pivot point 518 which allows upper body 516 to rotate between a generally vertical access position, as shown, and a generally horizontal operational position, such as is shown in FIG. 2.

Figure 18:
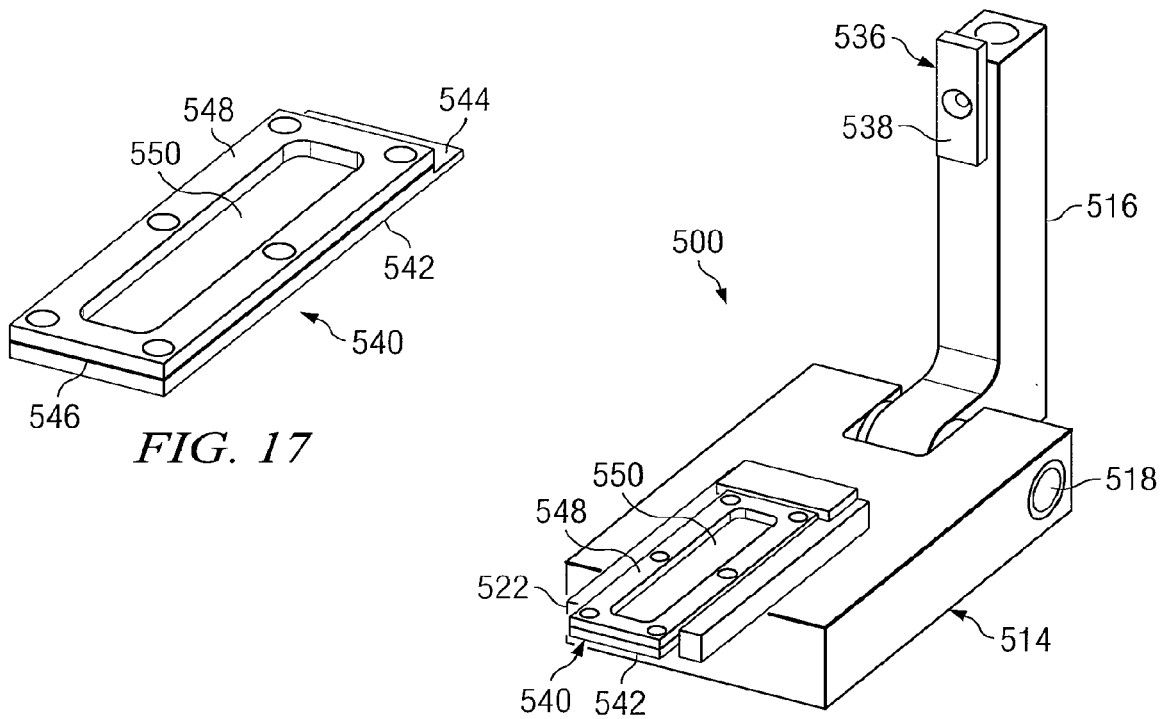
FIG. 18 shows an electroporation system with a conductive slide installed within conductive slide mounting structure according to the teachings of the present disclosure.

Electroporation system 500 further includes conductive slide mounting structure 522 attached to lower body 514. Conductive slide mounting structure 522 is preferably designed to mechanically and conductively interface with a conductive slide such as electrode slide 540 as shown in FIG. 18. In the present embodiment conductive slide mounting structure 522 includes a groove 526 formed to receive a conductive slide 540. Groove 526 is formed between first side wall 528 and second side wall 530. Groove 526 also includes an interface slot 524 formed to conductively interface with conductive slide 540. In preferred embodiments, interface slot 524 may include a spring contact for conductively interfacing with a conductive slide. The front side of groove 526 includes a rounded edge 532 to facilitate loading and unloading of slides thereon.

Upper housing 516 includes upper electrode 536 attached thereto which may be selectively removable for replacement or sanitization. Upper electrode 536 preferably includes contact surface 538 (which may also be referred to as an upper electrode contact surface). Upper electrode contact surface 538 is preferably sized and shaped to correspond with a contact surface of an electroporation slide. In the present embodiment contact surface 538 has a generally rectangular shape to correspond with the generally rectangular contact surface area of electrode slide 540.

Figure 17:
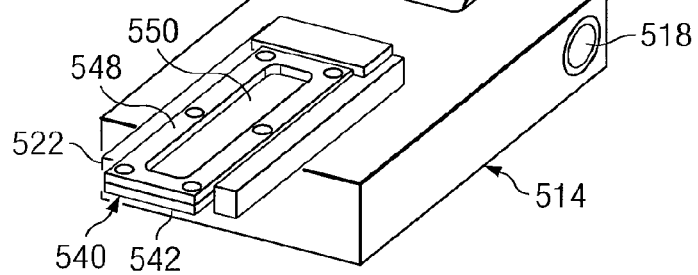
FIG. 17 shows a conductive slide according to the teachings of the present disclosure.

Now referring to FIG. 17, a conductive slide 540 is shown. Conductive slide 540 includes base 542 having interface tab 544 extending therefrom. Interface tab 544 is preferably sized to insert within interface slot 524 to allow a desired electric pulse to pass through the conductive portions of slide 540 and also to make a mechanical connection therewith. Slide 540 further includes ring element 548 attached thereto. Ring element 548 defines the shape and size of contact surface 550 (which may also be referred to as a lower electrode contact surface) and further forms a well thereon for depositing a sample. Ring element 548 may be secured onto slide 540 using any suitable attachment or fastening method and may further be constructed of a nonconductive material.

Slide 540 may be used with any sample but is particularly applicable for use with adherent cells that may be developed, grown, or otherwise processed on the surface 550 of slide 540. Such processing may take place both before and/or after the electroporation of the sample. In some operations, cells may be plated onto contact surface in normal growth media and cultured to allow time for cells to attach. Cells would then be prepared for electroporation by first washing the cells in sterile phosphate-buffered saline followed by the addition of electroporation buffer containing a transfectant (siRNA, other nucleic acid, etc.). After the applied electroporation event, cells would be allowed to rest and recover for a desired amount of time, in many instances five to twenty minutes. The buffer may then be removed and fresh media added to the cells. Cells may then be cultured for a predetermined period of time appropriate for the particular assay.

Base 542 may be a glass slide that includes a conductive layer 546 formed on the top surface of the slide. In one embodiment, layer 546 is a conductive material such as indium-tin-oxide (ITO). In other embodiments, layer 546 may be a gas permeable membrane such as aluminum oxide membrane filters.

FIG. 18 shows slide 540 installed within conductive slide mounting structure 522. Slide mounting structure 522 interfaces with slide 540 such that an electric pulse may be conducted to layer 546 and, in turn, to contact surface 550. In operation, a sample may be provided on contact surface 550 and upper body may then be positioned such that upper electrode contact surface 538 contacts the sample and is positioned at a desired gap width. Layer 546 and electrode 536 are further in conductive connection with a pulse generator (as shown in FIG. 5) operable to provide a desired pulse for a desired duration.

Although the disclosed embodiments have been described in detail, it should be understood that various changes, substitutions and alterations can be made to the embodiments without departing from their spirit and scope.

What is claimed is:

1. An electrode array system for electroporation comprising:
    a plurality of sample contact surfaces, each of the plurality of sample contact surfaces operable to hold an electroporation sample;
    the plurality of sample contact surfaces electrically connected to receive an electric pulse from a pulse generator wherein the electric connection is operable to provide electric current to electroporate the electroporation sample present on each of the sample contact surfaces;
    the plurality of sample contact surfaces disposed on an electrode base; and the plurality of sample contact surfaces associated with a corresponding electrode array.

2. The electrode array system of claim 1 wherein the electrode base is a 96 sample base.

3. The electrode array system of claim 1, further comprising one or more component selected from a monitoring system, a computer system and computer software.

4. The electrode array system of claim 1, wherein the shape of the sample contact surfaces is flat.

5. The electrode array system of claim 1, wherein the shape of the sample contact surfaces is circular.

6. The electrode array system of claim 1, wherein the shape of the sample contact surfaces is non-flat.

7. The electrode array system of claim 1, wherein the shape of the sample contact surfaces is non-circular.

* * * * *